US 6,750,367 B2

(12) United States Patent
Adkins et al.

(10) Patent No.: US 6,750,367 B2
(45) Date of Patent: Jun. 15, 2004

(54) TETRALIN ISOCYANATES

(75) Inventors: Rick L. Adkins, Hurricane, WV (US); Harold R. Parsons, Wheeling, WV (US)

(73) Assignee: Bayer Polymers LLC, Pittsburgh, PA (US)

( * ) Notice: Subject to any disclaimer, the term of this patent is extended or adjusted under 35 U.S.C. 154(b) by 38 days.

(21) Appl. No.: 10/142,289

(22) Filed: May 9, 2002

(65) Prior Publication Data

US 2003/0212160 A1 Nov. 13, 2003

(51) Int. Cl.⁷ .............................................. C07C 267/00
(52) U.S. Cl. .................... 560/358; 560/330; 560/336; 560/338; 560/360
(58) Field of Search .................. 560/330, 336, 560/338, 358, 360

(56) References Cited

U.S. PATENT DOCUMENTS

| | | | |
|---|---|---|---|
| 2,628,964 A | * 2/1953 | Scalera et al. | 548/437 |
| 2,948,611 A | 8/1960 | Barney | |
| 3,971,804 A | 7/1976 | Widdig et al. | |
| 3,975,418 A | * 8/1976 | Duerr | 560/358 |
| 4,239,856 A | 12/1980 | Rowton | 521/118 |
| 4,256,849 A | 3/1981 | Ick et al. | 521/129 |
| 4,261,852 A | 4/1981 | Carroll et al. | 528/59 |
| 4,365,025 A | 12/1982 | Murch et al. | 521/159 |
| 4,379,767 A | * 4/1983 | Alexanian et al. | 560/337 |
| 4,395,369 A | * 7/1983 | Henderson et al. | 560/337 |
| 4,478,960 A | 10/1984 | Buethe et al. | 521/160 |
| 4,876,292 A | 10/1989 | Milliren | 521/159 |
| 4,945,117 A | 7/1990 | Gansen et al. | 521/99 |
| 5,070,114 A | 12/1991 | Watts et al. | 521/159 |
| 5,246,935 A | 9/1993 | Jeppesen et al. | |
| 5,369,138 A | 11/1994 | Gansen | 521/159 |
| 5,521,225 A | 5/1996 | Gerber et al. | 521/155 |

FOREIGN PATENT DOCUMENTS

| | | |
|---|---|---|
| GB | 951549 | 3/1964 |
| WO | 02/28843 | 4/2002 |

OTHER PUBLICATIONS

Siefken, Werner: "Mono– Und Polyisocyanate" Annalen Der Chemie, Justus Liebigs, No. 562, 1949, pp. 75–136, XP009015174, pp. 78–80 and 88; p. 94, lines 27–36 and p. 119, the table, entries 7 and 8. (1949).

* cited by examiner

*Primary Examiner*—John M. Cooney, Jr.
(74) *Attorney, Agent, or Firm*—Joseph C. Gil; Noland J. Cheung; John E. Mrozinski, Jr.

(57) ABSTRACT

The present invention relates to novel aromatic isocyanates obtained by partially hydrogenating naphthalene as well as the processes for preparing the same, and to their use as an isocyanate component in the production of polyurethanes.

2 Claims, No Drawings

TETRALIN ISOCYANATES

FIELD OF THE INVENTION

The present invention relates to novel aromatic isocyanates obtained by partially hydrogenating naphthalene as well as the processes for preparing the same, and to their use as an isocyanate component in the production of polyurethanes.

BACKGROUND OF THE INVENTION

Among the organic polyisocyanates of commercial and economic significance as starting materials for polyurethanes, both rigid and flexible foams, in particular flexible foams, mixtures of diphenylmethane diisocyanate (MDI), polyphenylene polymethylene polyisocyanates, prepolymers based on such materials, and toluene diisocyanate (TDI) are known to be suitable for preparing flexible foams. See, for example, U.S. Pat. Nos. 4,239,856, 4,256,849, 4,261,852 and 4,365,025, 5,070,114, 4,478,960, 4,945,117, 5,369,138, 4,876,292, 5,521,225.

Allophanate modified isocyanates are also known in the art. Various isocyanates containing allophanate groups and processes for their production are disclosed in, for example, U.S. Pat. Nos. 4,738,991, 4,866,103, 5,319,053 and 5,319,054, and European Patents 0,031,650 and 0,393,903.

An improved isocyanate was required to have improved physical properties over TDI, so it needed to be liquid (an advantage over MDI) and have a vapor pressure higher than TDI (hence it's higher molecular weight structure). Surprisingly, such a foam also exhibited improvement in foam properties.

Foams of varying hardness, reasonable physical properties and good humid aged compression sets can be formulated with the present tetralin isocyanates. Physical properties such as elongation and tear were improved.

SUMMARY OF THE INVENTION

The present invention relates to isocyanates corresponding to the formula:

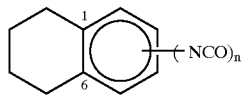

wherein
n is a number from 1 to 2.

DETAILED DESCRIPTION OF THE INVENTION

The present invention relates to isocyanates corresponding to the formula:

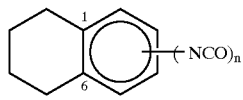

wherein n is 1 or 2.
When n=1, the isocyanate can be 2- or 3-tetralin isocyanate. When n=2, the isocyanate can be 2,3-tetralin diisocyanate, 2,4-tetralin diisocyanate, 3,4-tetralin diisocyanate, 2,5-tetralin diisocyanate, or mixtures thereof.

The novel isocyanates of the present invention are produced by reacting tetralindiamine with phosgene. The starting diamines can be produced by processes already known (See "Nitrobenzene and Nitrotoluenes", Kirk-Othmer Encyclopedia of Chemical Technology, 4$^{th}$ ed, vol 17, 1996 and "Diaminotoluenes", ibid, vol 2, 1992.). For example, tetrahydronaphthalene (tetralin) can be converted to the diamine by catalytic hydrogenation. In particular, the reaction of tetralin with nitric acid results in dinitrotetralin, which then is catalytically hydrogenated to give tetralindiamine.

Tetrahydronaphthalene is a commercially available product, which can be made by partially hydrogenating naphthalene.

The above-diamine is converted to the isocyanate of the present invention by reacting it with phosgene. Phosgene may be employed in either liquid or gaseous form, preferably liquid form. The tetralindiamine is dissolved in a mixture of diglyme/1,2-dichlorobenzene and added to the phosgene solution. The temperature of the reaction medium ranges from about 90 to 190° C., preferably from 110 to 170° C.

The tetralin di or isocyanate can also be made from the amine using phosgene free approaches such as urethane splitting.

The novel isocyanate of the present invention may be used in the same fields as aromatic polyisocyanates of prior art have been used. For example, it can be used in the fields such as polyurethane by reacting various compounds, including polymers, containing active hydrogen groups such as polyols, as well as intermediates, for producing other novel compounds or polymers, and so on. The new isocyanates according to the present invention may be used instead of TDI and/or MDI in all processes for the production of polyurethanes using these known polyisocyanates.

EXAMPLES

The invention is described in more detail with the aid of the following examples.

Example 1
Preparation of Tetralin Diamine

A 2,000 g quantity of nitric acid solution (39.2% by weight in sulfuric acid) was added to a 5 liter flask. 1,2,3,4-Tetrahydronaphthalene (tetralin) was slowly added, maintaining a temperature of 70° C. The reaction mixture was stirred at 70° C. for three (3) hours, then washed with water (2×1L) and 10% sodium bicarbonate (2×0.5L). The dinitrotetralin was dried and reacted with hydrogen at 1,500 psig and 160° C. for two (2) hours to give tetraline diamine.

Example 2
Preparation of Tetralin Diisocyanate 1,2-dichlorobenzene(1.5L) was cooled to 0° C. and phosgene added at a rate of 3 moles/hour for 1.8 hours. Tetralin diamine (150 g) was dissolved in a 50:50 mixture of diglyme/1,2-dichlorobenzene and added to the phosgene solution. The reaction solution was slowly heated to 135° C. and held at that temperature for 1 hour. The resulting mixture was purged with nitrogen and the solvent was vacuum distilled (134–136° C. at 2.7 mmHg) to give a light yellow liquid with a % NCO content of 34.5.

Example 3
Polyurethane Foams Using Tetralin Diisocyanate

The table below illustrates the results obtained when tetralin diisocyanate was used in a standard TDI foam formulation. TDI was also foamed to give a control sample. The polyol used is a glycerin/propylene glycol based polyol with a hydroxyl number of 56. The catalyst is a mixture comprised of Dabco T-9, Dabco T-12, and Polycat 70. L-620 is a silicone surfactant.

As can be seen, the tensiles were very similar. In addition, the tetralin diisocyanate showed a 24% improvement in both the elongation and tear strength.

TABLE 1

| ISO Index | TDI 100 | Tetralin Diisocyanate 100 |
|---|---|---|
| Formulations: | | |
| Polyol | 100 | 100 |
| Water | 4.00 | 4.40 |
| L-620 | 0.8 | 0.8 |
| Catalyst | 0.5 | 1.0 |
| Foam Properties: | | |
| Density, pcf | 1.30 | 1.31 |
| Tensile, psi | 17.7 | 17.3 |
| Elongation, % | 168 | 208 |
| Tears, lbs/in | 1.72 | 2.13 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Isocyanates corresponding to the formula:

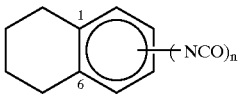

wherein n is 1 or 2.

2. A process for preparing isocyanates corresponding to the formula:

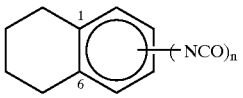

wherein n is 2 comprising the steps of:
a) reacting 1,2,3,4-tetrahydronaphthalene with nitric acid to produce dinitrotetralin;
b) catalytically hydrogenating dinitrotetralin to produce tetralin diamine.
c) phosgenating tetralindiamine to produce a resulting product; and
d) distilling said resulting product.

* * * * *